United States Patent [19]

Fan

[11] Patent Number: 4,640,306

[45] Date of Patent: Feb. 3, 1987

[54] FLUID FLOW REGULATOR FOR INTRAVENOUS FEEDING DEVICE

[75] Inventor: Cheng-Kuo Fan, Kaohsiung, Taiwan

[73] Assignee: Liang-Jr Lee, Kaohsiung, Taiwan

[21] Appl. No.: 841,255

[22] Filed: Mar. 19, 1986

[51] Int. Cl.[4] .................. F16K 31/22; F16K 33/00

[52] U.S. Cl. ........................... 137/390; 137/433; 137/399; 251/342; 251/347; 251/349; 604/254

[58] Field of Search .............. 137/390, 399, 430, 433; 251/340, 342, 347, 349; 604/127, 251, 254

[56] References Cited

U.S. PATENT DOCUMENTS

| | | | |
|---|---|---|---|
| 1,205,410 | 11/1916 | Tenney | 604/127 |
| 3,227,173 | 1/1966 | Bernstein | 604/254 |
| 3,465,784 | 9/1969 | Cofoid | 137/390 |
| 4,055,176 | 10/1977 | Lundquist | 604/254 |
| 4,056,116 | 11/1977 | Carter et al. | 251/342 |

Primary Examiner—George L. Walton

[57] ABSTRACT

A fluid flow regulator includes a resilient hollow sealing body which is fitted in the bottom part of a liquid housing adjacent to a tubular outlet end and which has a central through-hole to communicate to one another the chamber of the housing and the outlet end. An annular flange which extends from the top of the sealing body toward the through-hole forms a valve seat against which a float valve can be efficiently and tightly seated. A movable tube is inserted in the tubular end to be used to manually release the float valve from the valve seat.

5 Claims, 6 Drawing Figures

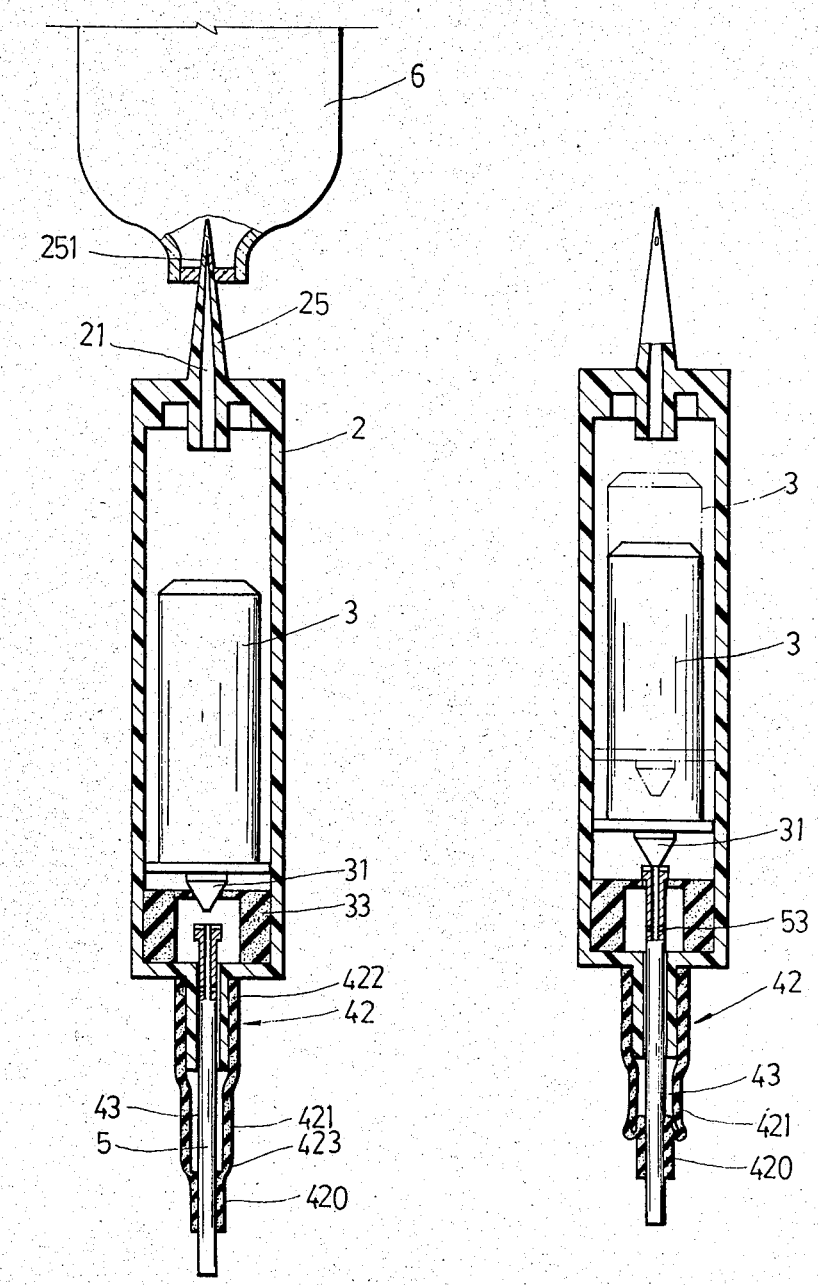

FLUID FLOW REGULATOR FOR INTRAVENOUS FEEDING DEVICE

BACKGROUND OF THE INVENTION

This invention relates to a fluid flow regulator for an intravenous feeding device and particularly to a fluid flow regulator including an elastic sealing body which has a fluid passage directed to the outlet of a medication container and forms a valve seat in the fluid passage against which a float plug can be seated.

Various forms of fluid flow regulators to be incorporated in an intravenous feeding device have existed in the prior art. Examples of such fluid flow regulators are disclosed in many patents, such as, U.S. Pat. Nos. 4,055,176, 1,205,410, 4,096,879, 3,227,173, etc. Generally, the fluid flow regulator includes a housing having an inlet and an outlet through which the medication liquid flows, and a float valve to shut off the outlet of the housing when the housing runs out of liquid. The float valve is seated against a valve seat formed at the outlet by a suction force created downstream of the valve seat when the housing is empty of liquid. In common practice, the outlet of the housing is a conduit-like member extending from the bottom of the housing and the conduit-like member forms itself a valve seat at its topmost part. Such a valve seat is not resilient and, therefore, an efficient seal between the valve seat and the float valve can not be obtained if the suction force is not enough to hold a large float valve tightly against the valve seat.

Moreover, there is an inconvenience caused by most conventional regulators wherein a period of time is needed for the medication to reach the veins of the patient since the float valve which seats against the valve seat is released therefrom only when the medication liquid achieves a sufficient buoyancy to float the float valve.

SUMMARY OF THE INVENTION

An object of the invention is to provide a fluid flow regulator of the above-mentioned type with a resilient valve seat so that an efficient seal can be achieved between the valve seat and the float valve.

Another object of the invention is to provide a fluid flow regulator of the above-mentioned type with a means to release manually the float valve from the valve seat so that the medication liquid can flow into the vein of the patient at an earlier time.

The present invention provides a fluid flow regulator which includes a resilient hollow sealing body fitted in the bottom part of a liquid housing adjacent to the tubular outlet end, wherein the body has a central through-hole therein directed from the chamber confined by the housing to the tubular outlet end, and an annular flange projecting toward the through-hole at the top side of the sealing body to form a valve seat. The valve seat so formed is resilient so that it can provide an efficient seal with the float body when the float body seats against it. The resilient sealing body has a peripherial surface and a bottom annular surface sealingly and frictionally abutting against the inner surfaces of the housing. Preferably, the body is axially thick.

The invention further provides a tube inserted movably in the tubular outlet end and adapted to push manually the float valve from the valve seat. The top of the tube extends to the through-hole of the resilient body to communicate therewith. An elastic connecting sleeve is provided having an upper end secured to the tubular outlet end and a lower end secured to the tube. The elastic sleeve is extensible and retractable in axial direction relative to the tubular outlet end to allow the tube to move in the tubular outlet end.

The elastic connecting sleeve may be in the form of a bellows. Alternatively, the elastic connecting sleeve may be an elastic stepped hollow body of different cross-sections having a first portion sleeved tightly around the tubular outlet end, a third portion sleeved tightly around the tube, and a second portion between the first and third portions surrounding the tube with a space left between the tube and the second portion.

The float body is cylindrical and has flanges radially extending from the periphery of the body to center the body. The plug portion of the float body is substantially cone-shaped.

The present exemplary preferred embodiments will be described in detail with reference to the following drawings.

BRIEF DESCRIPTION OF THE DRAWINGS

FIG. 3 is a sectional view of an alternative fluid flow regulator embodying the present invention;

FIG. 4 is a sectional view of the fluid flow regulator of FIG. 3 in which the float valve is lifted by the movable tube;

DETAILED DESCRIPTION OF THE PREFERRED EMBODIMENTS

Figures 1, 2:
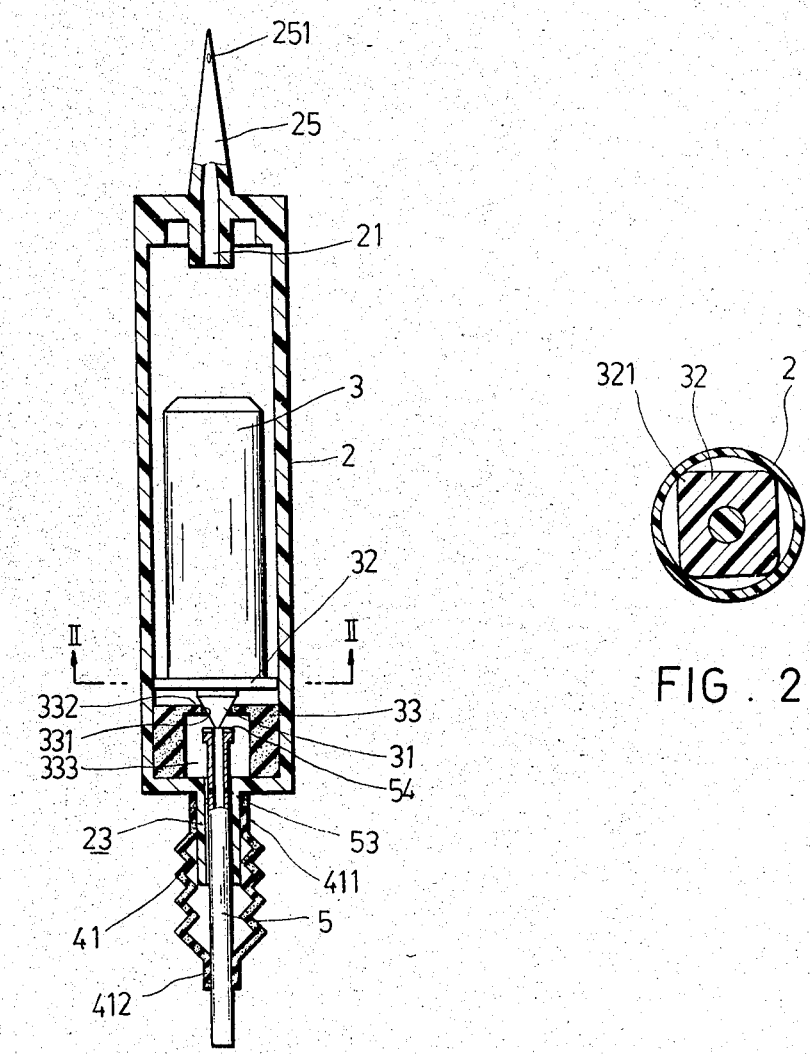
FIG. 1 is a sectional view of a fluid flow regulator according to the present invention.
FIG. 2 is a sectional view taken along line II—II of FIG. 1.

Referring to FIGS. 1 and 2, a first embodiment of a fluid flow regulator incorporating the present invention includes a cylindrical liquid housing 2 having a spike 25 projecting from the top thereof to be used to vent an intravenous liquid bottle, and an inlet passage 21 extending along the spike 25 and opening at 251 to admit the intravenous liquid from the bottle.

At the bottom side of the housing 2 is an outlet tubular end 23 in which is inserted movably a tube 5 having an open end 54 and openings 53 in the wall thereof. The top portion of the tube 5 extends into the through-hole 333 of the sealing body 33 to communicate therewith. The tube 5 may be either a short tube which is to be connected to a flexible tube with a terminating needle (not shown), or a tube of one piece with the flexible tube. There is an elastic connecting sleeve 41 sleeved around the tubular outlet end 23 to connect the tube 5 to the tubular outlet end 23 so that the tube 5 is not released from the tubular outlet end 23. The upper end 411 of the sleeve 41 is fixed to the outlet tubular end 23 of the housing 2 and the lower end 412 of the sleeve 41 is fixed to the tube 5. The elastic sleeve 41 is in the form of a bellows which can be retracted or stretched out axially relative to the tubular outlet end 23 of the housing 2 so as to allow the tube 5 to move in the tubular outlet end 23.

There is a resilient hollow sealing body 33 stuffed into the bottom side of the housing 2. Preferably, the sealing body 33 is axially thick so that it possesses a large peripheral surface to sealingly and frictionally abut aginst the wall of the housing 2, whereby the sealing body can be held in position and kept in an efficient fluid tight relationship with the inner surface of the housing 2. There is a central through-hole 333 in the sealing body 33 communicating the liquid chamber and the tubular outlet end 23, and an annular flange 332 projecting inwardly at the top side of the sealing body 33 to form a valve seat 331. The valve seat 331 so formed can abut tightly against the float body.

A cylindrical float body 3 is disposed in the housing 2 and includes a substantially rectangular guide plate portion 32 at its bottom side and a cone-shaped plug portion 31 extending from the central part of the bottom side of guide plate portion 32. The plug portion 31 can be seated on the valve seat 331 to shut off the opening of the annular flange 332 when the housing 2 is empty of liquid. The guide plate portion 32 has edge portions 321 in sliding contact with the inner surface of the wall of the housing 2 so as to center the float body 3 in the housing 2. As such, the plug portion 31 can project sealingly in the valve seat 331 when the housing 2 is empty of liquid.

In operation, the medication bottle is vented by the spike 25 and the medication is admitted in the housing 2. It is assumed that the plug portion 31 of the float body 3 is projecting in the valve seat 331 at the time when the medication is delivered into the housing 2. The plug portion 31 is released from the valve seat 331 by being pushed manually with the top end of the movable tube 5, thereby enabling the float body 3 to float by the buoyance of the liquid and enabling the medication to enter in the through-hole 333 of the sealing body 33. How the plug portion 31 is released from the valve seat 331 is illustrated in FIG. 4. When the float body 3 floats in the liquid by the buoyance of the liquid, the tube 5 can be released from hand. Since the movable tube 5 is provided to release the plug portion 31 manually, the medication liquid can flow to the vein of the patient without a lot of time being necessary to obtain sufficient buoyancy of the medication liquid to allow the float body to float.

The medication liquid entering the through-hole 333 of the sealing body 33 through the valve seat 331 flows into the tube 5 through the open top end 54 and the openings 53 and then is delivered to the flexible pipe directed to the vein of the patient. When the housing 2 is about to run out of liquid, the plug portion 31 of the float body 3 seats against the valve seat 331 by suction force created in the through-hole 333 of the sealing body 33, shutting off the opening defined by the valve seat 331.

Another embodiment of the fluid flow regulator is shown in FIGS. 3 and 4 in which elements which are of the same construction as those shown in FIG. 1 are represented by the same reference numerals. Numeral 6 designates a medication bottle. The movable tube 5 is inserted in the tubular outlet end 23 of the housing 2 and an elastic connecting sleeve 42 which is different from the sleeve 41 is sleeved around the tubular outlet end 23. The connecting sleeve 42 is a stepped sleeve body made of an elastic, flexible material such as rubber and has three portions 420, 421 and 422 of different cross-sections. The portion 422 is sleeved tightly on the tubular end portion 23 of the housing 2 and the portion 420 is sleeved tightly on the lower portion of the tube 5. The intermediate portion 421 surrounds the tube 5 with an annular space 43 left between the tube 5 and the portion 421.

When the tube 5 is moved upward to push the plug portion 31 of the float body 3, shoulder portion 423 of the connecting sleeve 42 is folded into the space 43 as is shown in FIG. 4. The folded shoulder portion 423 is frictionally held in position so that the tube 5 will not move down as long as no external force is applied to it. Consequently, one need not continue to lift the tube 5 to hold the plug portion 31 apart from the valve seat 331 until the float body 3 floats by the buoyance of the liquid. When the float body 3 floats, the tube 5 is pulled downward to its normal position. The elastic connecting sleeve 42 offers more convenient operation than the sleeve 41 of the former embodiment.

Figures 5, 6:
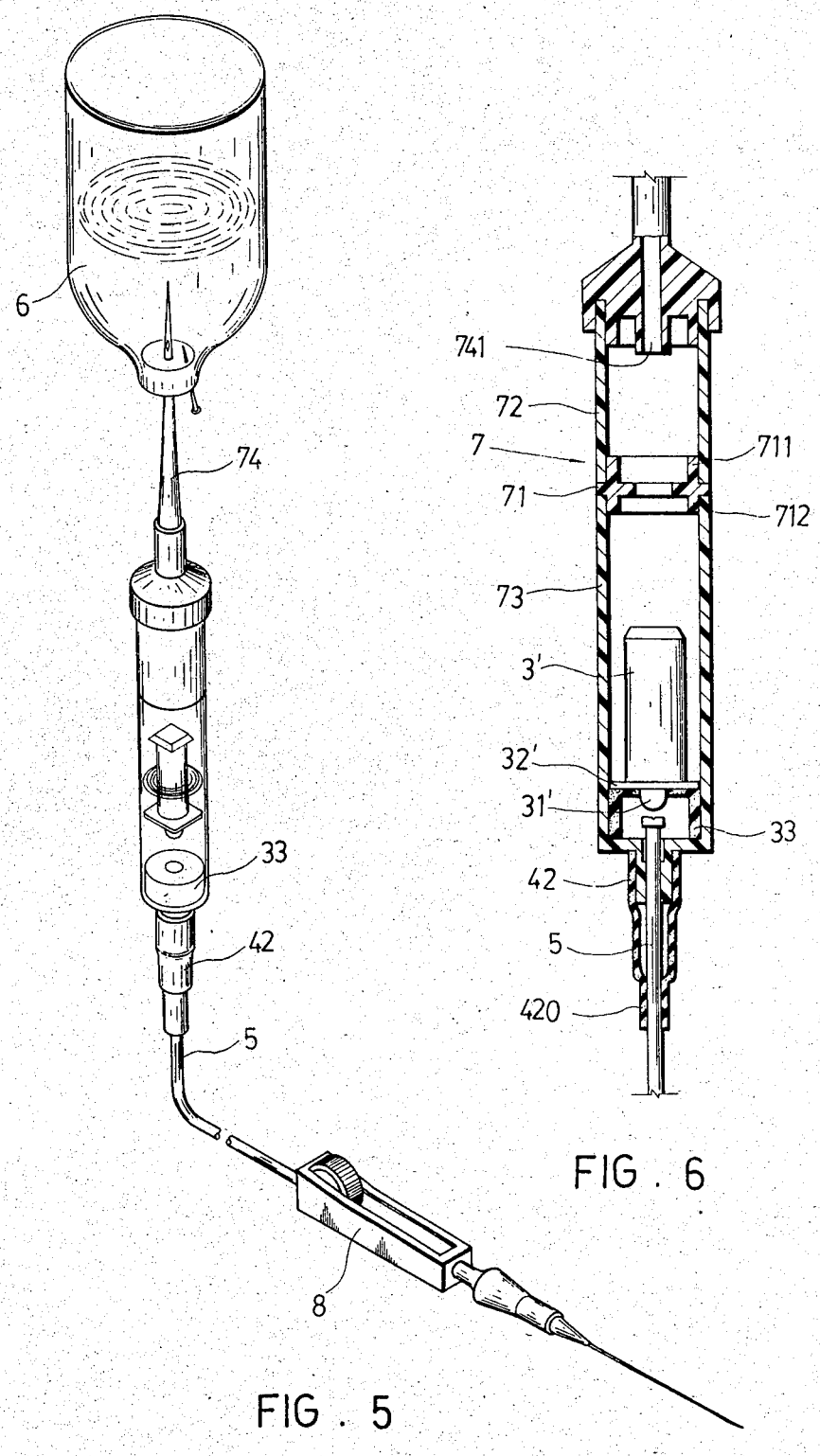
FIG. 5 is a perspective view of another alternative fluid flow regulator embodying the present invention.
FIG. 6 is a sectional view of the fluid flow regulator of FIG. 5.

Still another embodiment of the fluid flow regulator is shown in FIGS. 5 and 6 in which elements which are of the same construction as those shown in FIG. 1 are represented by the same reference numerals. This embodiment differs from the former embodiments in that it includes a housing 7 constituted of an upper housing component 72 made of a compressible material and a lower housing component 73 made of a transparent, rigid or semi-rigid material. The upper and lower housing components 72 and 73 are interconnected and intercommunicated by a hollow connector 71 to the ends of which are sealingly connected the upper and lower housing components 72 and 73.

The upper housing component 72 can be used as a pump for pumping the medication liquid from the bottle to the housing 7 by compressing it and allowing it to expand alternatingly. The regulator of this embodiment can be used in combination with a control device 8 by which the flow rate of the medication liquid can be adjusted.

With the invention thus explained, it is apparent that various modifications and variations can be made without departing from the scope of the invention. It is therefore intended that the invention be limited as indicated in the appended claims.

What I claim is:

1. A fluid flow regulator for intravenous feeding device comprising:
   a cylindrical housing defining a liquid chamber having a top inlet end and a bottom tubular outlet end;
   a resilient hollow sealing body fitted in the bottom part of the housing adjacent to the tubular outlet end, the body having a central through-hole therein directed from the chamber to the tubular outlet end, and an annular flange projecting toward the through-hole at the top side of the sealing body, the annular flange forming a valve seat;
   a float body disposed in the chamber and having a bottom plug portion to seat against the valve seat;
   a tube inserted movably in the tubular outlet end for communicating the intravenous fluid flow, the top of the tube extending to the through-hole of the resilient body to communicate therewith; and
   an elastic connecting sleeve having an upper end secured to the tubular outlet end and a lower end being directly secured to the tube with said tube extending through said lower end, the elastic sleeve being extensible and retractable in an axial direction relative to the tubular outlet end as said tube moves in said axial direction.

2. A fluid flow regulator as claimed in claim 1, wherein the sealing body is axially thick and has a peripherial surface and a bottom annular surface sealingly abutting against the inner surfaces of the housing.

3. A fluid flow regulator as claimed in claim 1, wherein the elastic connecting sleeve is in the form of a bellows.

4. A fluid flow regulator as claimed in claim 1, wherein the elastic connecting sleeve is an elastic stepped hollow body of different cross-section having a first portion sleeved tightly around the tubular outlet and, a third portion sleeved tightly around the tube, and a second portion between the first and third portions surrounding the tube with a space left between the tube and the second portion.

5. A fluid flow regulator as claimed in claim 1, wherein the float body is cylindrical and has flanges radially extending from the periphery of the body to center the body, and the plug portion of the float body is substantially cone-shaped.

* * * * *